(12) United States Patent
Wang et al.

(10) Patent No.: US 8,551,310 B2
(45) Date of Patent: Oct. 8, 2013

(54) METHOD FOR MAKING A NANO-COMPOSITE GAS SENSOR

(75) Inventors: Li-Chun Wang, Taoyuan County (TW);
Tseng-Hsiung Su, Tainan (TW);
Shang-Ren Yang, Yilan County (TW);
Cheng-Long Ho, New Taipei (TW);
Han-Wen Kuo, New Taipei (TW);
Kea-Tiong Tang, Hsinchu (TW)

(73) Assignee: Chung-Shan Institute of Science and Technology, Armaments Bureau, Dept. of National Defense (TW)

( * ) Notice: Subject to any disclaimer, the term of this patent is extended or adjusted under 35 U.S.C. 154(b) by 101 days.

(21) Appl. No.: 13/328,115

(22) Filed: Dec. 16, 2011

(65) Prior Publication Data

US 2013/0152349 A1 Jun. 20, 2013

(51) Int. Cl.
*G01N 27/26* (2006.01)

(52) U.S. Cl.
USPC ............................ 204/431; 977/705; 977/721

(58) Field of Classification Search
USPC ................... 204/431; 977/705, 712, 720, 721
See application file for complete search history.

(56) References Cited

U.S. PATENT DOCUMENTS

| | | | |
|---|---|---|---|
| 7,918,989 B2 * | 4/2011 | Kang et al. ................ 205/782 |
| 2005/0209392 A1 * | 9/2005 | Luo et al. .................. 524/496 |
| 2008/0142361 A1 * | 6/2008 | Han et al. .................. 204/400 |
| 2011/0081724 A1 * | 4/2011 | Swager et al. ............... 436/57 |

\* cited by examiner

*Primary Examiner* — Seahvosh Nikmanesh
*Assistant Examiner* — Reema Patel

(57) ABSTRACT

There is disclosed a method for making a nano-composite gas sensor. At first, there is provided a substrate. Then, electrodes are provided on the substrate in an array. Finally, a gas-sensing membrane is provided on the electrodes. The gas-sensing membrane includes a nano-conductive film and a peptide film.

15 Claims, 3 Drawing Sheets

METHOD FOR MAKING A NANO-COMPOSITE GAS SENSOR

BACKGROUND OF INVENTION

1. Field of Invention

The present invention relates to a method for making a gas sensor and, more particularly, to a method for making a nano-composite gas sensor.

2. Related Prior Art

Disclosed in U.S. Pat. No. 6,759,010 is an sensor array. The resistances of the sensors are used to form a fingerprint-like pattern for sensing gases. The sensing of the gases is important in the industry such as the semiconductor industry in which ammonia is used together with many other gases. The sensor array includes more than two polymers on an electrode before the electrode is connected to other electrodes. The sensor array provides a warning when it contacts hazardous gas.

As disclosed in U.S. Pat. No. 6,929,735, an ion-type polymer film is coated on electrodes of a sensor. The sensitivity of the gas sensor is good because gas directly reaches the electrodes.

As disclosed in U.S. Pat. No. 5,674,752, a gas-sensing module includes a single resistance-type sensor or multiple resistance-type sensors connected to one another. One or more conductive polymers are coated on the electrodes of the gas-sensing module. The resistances of the sensors change as the polymer coated on the electrodes expands to different extents as it absorbs the gas. Thus, a fingerprint-like pattern is formed for the sensing of the gas. This gas-sensing module can be used to detect DMMP.

Disclosed in U.S. Pat. No. 7,186,799 is an array of surface acoustic wave ("SAW") sensors. Changes in the frequencies of the SAW sensors are used to form a fingerprint-like pattern for sensing gases. The spirit is to increase the sensitivity by increasing the oscillation frequencies of the SAW sensors or coating the SAW sensors with an organic material. Thus, the frequencies of the SAW sensors change as the SAW sensors contact hazardous gas, and the SAW gas-sensing module provides a warning.

The use of the above-mentioned patents is not without problems. At first, in a composite manner, multiple peptides or a multi-component peptide is mixed with a nano-conductive material such as carbon black so that the conductive material is evenly suspended in the peptide-based mixture. Thus, a composite film is made. It is not without any problems to disperse the various peptides or the multi-component peptide in the solvent, the sorts of the peptides or the components of the peptide are limited.

Secondly, carbon black, a kind of zero-dimension material, is used as the nano-conductive material. Carbon black, which exhibits inadequate mechanical properties and deformability, cannot be recovered adequately. Therefore, the sensitivity and repeatability are inadequate.

Thirdly, to make the conventional arrays of sensors, various polymers are mixed with nano-conductive materials. The making of the sensors is not easy because of the compatibility of the polymer and nano-conductive material with the solvent.

The present invention is therefore intended to obviate or at least alleviate the problems encountered in prior art.

SUMMARY OF INVENTION

It is the primary objective of the present invention to provide a method for making a nano-composite gas sensor.

To achieve the foregoing objective, the method includes the steps of providing a substrate, providing electrodes on the substrate in an array, and providing a gas-sensing membrane on the electrodes, wherein the gas-sensing membrane includes a nano-conductive film and a peptide film.

In the method for making a nano-composite gas sensor, the substrate may include an insulating material coated on a metal, a semiconductor or a ceramic material.

In the method for making a nano-composite gas sensor, the semiconductor may be provided in the form of a silicon wafer.

In the method for making a nano-composite gas sensor, the electrodes may be made of gold, platinum, silver or aluminum.

In the method for making a nano-composite gas sensor, the electrodes may be fork-shaped, elongated or helical.

In the method for making a nano-composite gas sensor, the peptide film may be provided on the nano-conductive film.

In the method for making a nano-composite gas sensor, the nano-conductive film may be made of carbon nanotubes, carbon black, carbon balls and graphene.

In the method for making a nano-composite gas sensor, the carbon nanotubes may be evenly dispersed in MEK, IPA, $H_2O$ or PVA to provide a carbon nanotube-based mixture of 0.1 wt % to 2.0 wt % of carbon nanotubes.

Preferably, the carbon nanotube-based mixture includes 0.5 wt % to 1.0 wt % of carbon nanotubes.

In the method for making a nano-composite gas sensor, the peptide film may be made of a Beta-Amyloid (1-40), Human galectin-1 or Human albumin.

In the method for making a nano-composite gas sensor, the peptide film may be made by evenly dispersing peptide in Toluene, THF or $H_2O$ to provide a peptide-based mixture that includes 5 wt % to 50 wt % of peptide.

Preferably, the peptide-based mixture includes 10 wt % to 45 wt % of peptide.

In the method for making a nano-composite gas sensor, the step of providing the gas-sensing membrane may include the steps of providing the nano-conductive film by evenly dispersing carbon nanotubes in a solvent to provide a carbon nanotube-based mixture, providing the peptide film by evenly dispersing peptide in the solvent to provide a peptide-based mixture, evenly providing 1 to 3 μl of the carbon nanotube-based mixture on the electrodes, drying the carbon nanotube-based mixture in a vacuum oven at 50 to 70 degrees Celsius for 1 to 3 hours to form the nano-conductive film with a resistance of 1 to 10 KΩ, evenly providing 1 to 3 μl of the peptide-based mixture on the nano-conductive film, and drying the peptide-based mixture in a vacuum oven at 50 to 60 degrees Celsius for 1 to 4 hours to form the peptide film.

Alternatively, the step of providing the gas-sensing membrane may includes the steps of providing the nano-conductive film by evenly dispersing carbon nanotubes in a solvent to provide a carbon nanotube-based mixture, providing the peptide film by evenly dispersing peptide in the solvent to provide a peptide-based mixture, evenly providing 1 to 10 μl of the carbon nanotube-based mixture on the electrodes, drying the carbon nanotube-based mixture in a vacuum oven at 40 to 80 degrees Celsius for 1 to 5 hours to form the nano-conductive film with a resistance of 1 to 50 KΩ, evenly providing 1 to 10 μl of the peptide-based mixture on the nano-conductive film, and drying the peptide-based mixture in a vacuum oven at 40 to 60 degrees Celsius for 1 to 5 hours to form the peptide film.

In the method for making a nano-composite gas sensor, the solvent may be MEK, IPA, $H_2O$ or PVA.

Other objectives, advantages and features of the present invention will be apparent from the following description referring to the attached drawings.

BRIEF DESCRIPTION OF DRAWINGS

The present invention will be described via detailed illustration of the preferred embodiment referring to the drawings wherein.

DETAILED DESCRIPTION OF PREFERRED EMBODIMENT

Figure 1:
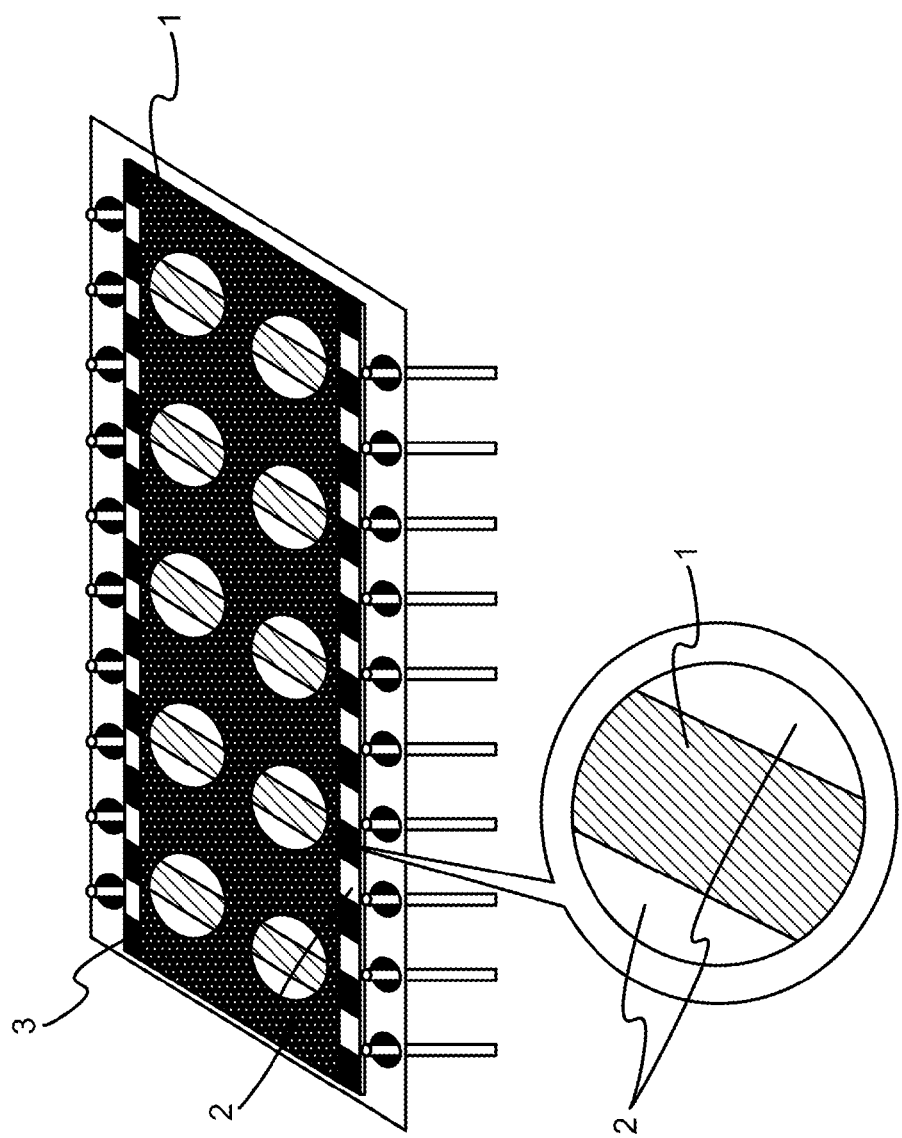
FIG. 1 is a perspective view of a nano-composite gas sensor made by a method according to the preferred embodiment of the present invention.

Referring to FIG. 1, there is shown a nano-composite gas sensor made by a method according to the preferred embodiment of the present invention.

The nano-composite gas sensor includes a substrate 1, electrodes 2 and a gas-sensing membrane 3.

The substrate 1 is a metal, a semiconductor or a ceramic material coated with an insulating material. The semiconductor may be provided in the form of a silicon wafer.

The electrodes 2 are provided on the substrate 1 in an array. The electrodes 2 may be made of gold, platinum, silver or aluminum, and preferably gold. Each of the electrodes 2 may be fork-shaped, elongated or helical, and preferably elongated.

The gas-sensing membrane 3 is provided on the electrodes 2 and the substrate 1. The gas-sensing membrane 3 includes a nano-conductive film 31 and a peptide film 32. The nano-conductive film 31 is used as a first layer of the gas-sensing membrane 3. As a second layer of the gas-sensing membrane 3, the peptide film 32 is provided on the nano-conductive film 31. The nano-conductive film 31 may be made of carbon nanotubes, carbon black, carbon balls, or grapheme, and preferably carbon nanotubes. The peptide film 32 may be made of Beta-Amyloid (1-40), Human galectin-1 or Human albumin, and preferably Beta-Amyloid (1-40).

In the method according to the preferred embodiment of the present invention, the nano-conductive film 31 is provided by evenly dispersing carbon nanotubes in a solvent. The peptide film 32 is provided by evenly dispersing peptide in a solvent.

Figure 2:
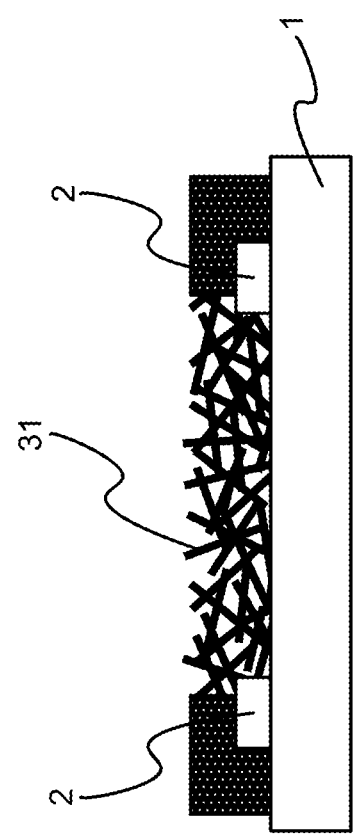
FIG. 2 is a cross-sectional view of a semi-product of the nano-composite gas sensor shown in FIG. 1.

Referring to FIG. 2, about 1 to 3 μl of carbon nanotube-based mixture is evenly provided on the electrodes 2, and dried in a vacuum oven at 50 to 70 degrees Celsius for 1 to 3 hours. Thus, formed is the nano-conductive film 31 with a resistance of 1 to 10 KΩ.

Figure 3:
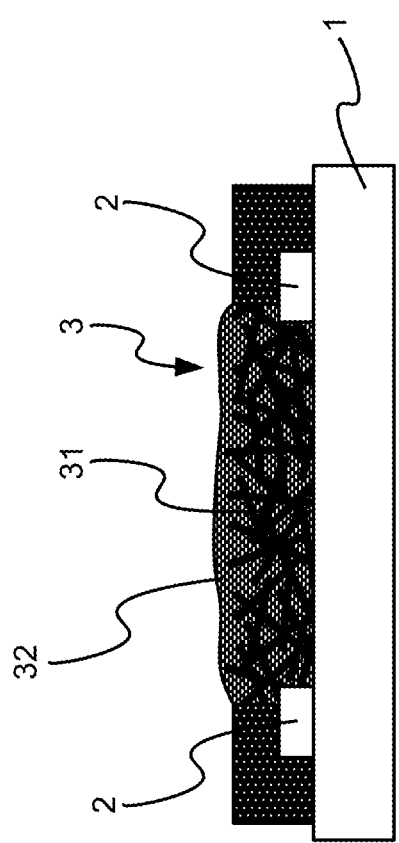
FIG. 3 is a cross-sectional view of the nano-composite gas sensor shown in FIG. 1.

Referring to FIG. 3, about 1 to 3 μl of peptide-based mixture is evenly provided on the nano-conductive film 31, and dried in a vacuum oven at 50 to 60 degrees Celsius for 1 to 4 hours. Thus, the peptide film 32 is formed on the nano-conductive film 31. Finally, the double-layered gas-sensing membrane 3 is made.

The carbon nanotubes are evenly dispersed in MEK, IPA, $H_2O$ or PVA. The carbon nanotube-based mixture includes 0.1 wt % to 2.0 wt % of carbon nanotubes. The carbon nanotube-based mixture preferably includes 0.5 wt % to 1.0 wt % of carbon nanotubes.

The peptide film 32 may be made of Beta-Amyloid (1-40), Human galectin-1 or Human albumin. The peptide film 32 is made by evenly dispersing peptide in Toluene, THF or $H_2O$. The peptide-based mixture includes 5 wt % to 50 wt % of peptide. The peptide-based mixture preferably includes 10 wt % to 45 wt % of peptide.

Thus, the result could improve the sensitivity and detection limit of chemiresistive gas sensor, and reduce the time of sensing. It can be made in the form of a microarray-type gas sensor or on a silicon wafer substrate to detect various gases. Thus, a double-layered gas-sensing membrane is made of the nano-conductive film 31 and the peptide film 32 that contains multiple components. Furthermore, as there may be various combinations of the nano-conductive film 31 with the peptide film 32, the composite gas sensor may further be used in a microarray-type gas sensor.

Alternatively, to make the nano-conductive film 31, carbon nanotubes are evenly dispersed in a solvent, thus providing carbon nanotube-based mixture. About 1 to 10 μL of the carbon nanotube-based mixture is evenly provided on the electrodes 2, and dried in a vacuum oven at 40 to 80 degrees Celsius for 1 to 5 hours. Thus, formed is the nano-conductive film 31 with a resistance of 1 to 50 KΩ.

To make the peptide film 32, peptide is evenly dispersed in another solvent, thus providing peptide-based mixture. About 1 to 10 μl of the peptide-based mixture is evenly provided on the nano-conductive film 31, and dried in a vacuum oven at 40 to 60 degrees Celsius for 1 to 5 hours. Thus, the peptide film 32 is formed on the nano-conductive film 31. Finally, the double-layered gas-sensing membrane 3 is made.

As discussed above, the method of the present invention is used to make a nano-composite membrane by covering the double-layered membrane 3, which consists of the nano-conductive film 31 and the peptide film 32, on the electrodes 2 provided on the substrate 1. The nano-composite membrane can be used to detect various gases. The detection limit of chemiresistive gas sensor is improved. The process is simplified. The time required by the method is reduced. The sensitivity is increased. Moreover, the controllability and repeatability are improved.

The present invention has been described via the detailed illustration of the preferred embodiment. Those skilled in the art can derive variations from the preferred embodiment without departing from the scope of the present invention. Therefore, the preferred embodiment shall not limit the scope of the present invention defined in the claims.

The invention claimed is:

1. A method for making a nano-composite gas sensor including the steps of:
   providing a substrate;
   providing electrodes on the substrate in an array; and
   providing a gas-sensing membrane on the electrodes, wherein the gas-sensing membrane includes a nano-conductive film and a peptide film, wherein the peptide film is made of a material selected from the group consisting of Beta-Amyloid (1-40), Human galectin-1 and Human albumin.

2. The method for making a nano-composite gas sensor according to claim 1, wherein the substrate includes an insulating material coated on a material selected from the group consisting of metal, semiconductor and ceramic materials.

3. The method for making a nano-composite gas sensor according to claim 2, wherein the semiconductor is provided in the form of a silicon wafer.

4. The method for making a nano-composite gas sensor according to claim 1, wherein the electrodes are made of a material selected from the group consisting of gold, platinum, silver and aluminum.

5. The method for making a nano-composite gas sensor according to claim 1, wherein the electrodes are made of a configuration selected from the group consisting of fork-shaped, elongated and helical.

6. The method for making a nano-composite gas sensor according to claim 1, wherein the peptide film is provided on the nano-conductive film.

7. The method for making a nano-composite gas sensor according to claim 1, wherein the nano-conductive film is made of a material selected from the group consisting of carbon nanotubes, carbon black, carbon balls and graphene.

8. The method for making a nano-composite gas sensor according to claim 7, wherein the carbon nanotubes are evenly dispersed in a solvent selected from the group consisting of MEK, IPA, $H_2O$ and PVA to provide a carbon nanotube-based mixture of 0.1 wt % to 2.0 wt % of carbon nanotubes.

9. The method for making a nano-composite gas sensor according to claim 7, wherein the carbon nanotubes are evenly dispersed in a solvent selected from the group consisting of MEK, IPA, $H_2O$ and PVA to provide a carbon nanotube-based mixture that includes 0.5 wt % to 1.0 wt % of carbon nanotubes.

10. The method for making a nano-composite gas sensor according to claim 1, wherein the peptide film is made by evenly dispersing peptide in a solvent selected from the group consisting of Toluene, THF and $H_2O$ to provide a peptide-based mixture that includes 5 wt % to 50 wt % of peptide.

11. The method for making a nano-composite gas sensor according to claim 1, wherein the peptide film is made by evenly dispersing peptide in a solvent selected from the group consisting of Toluene, THF and $H_2O$ to provide a peptide-based mixture that includes 10 wt % to 45 wt % of peptide.

12. The method for making a nano-composite gas sensor according to claim 1, wherein the step of providing the gas-sensing membrane includes the steps of:
   providing the nano-conductive film by evenly dispersing carbon nanotubes in a solvent to provide a carbon nanotube-based mixture; providing the peptide film by evenly dispersing peptide in the solvent to provide a peptide-based mixture;
   evenly providing 1 to 3 μL of the carbon nanotube-based mixture on the electrodes;
   drying the carbon nanotube-based mixture in a vacuum oven at 50 to 70 degrees Celsius for 1 to 3 hours to form the nano-conductive film with a resistance of 1 to 10 KΩ;
   evenly providing 1 to 3 μl of the peptide-based mixture on the nano-conductive film; and
   drying the peptide-based mixture in a vacuum oven at 50 to 60 degrees Celsius for 1 to 4 hours to form the peptide film.

13. The method for making a nano-composite gas sensor according to claim 12, wherein the solvent is selected from the group consisting of MEK, IPA, $H_2O$ and PVA.

14. The method for making a nano-composite gas sensor according to claim 1, wherein the step of providing the gas-sensing membrane includes the steps of:
   providing the nano-conductive film by evenly dispersing carbon nanotubes in a solvent to provide a carbon nanotube-based mixture;
   providing the peptide film by evenly dispersing peptide in the solvent to provide a peptide-based mixture;
   evenly providing 1 to 10 μL of the carbon nanotube-based mixture on the electrodes;
   drying the carbon nanotube-based mixture in a vacuum oven at 40 to 80 degrees Celsius for 1 to 5 hours to form the nano-conductive film with a resistance of 1 to 50 KΩ;
   evenly providing 1 to 10 μl of the peptide-based mixture on the nano-conductive film; and
   drying the peptide-based mixture in a vacuum oven at 40 to 60 degrees Celsius for 1 to 5 hours to form the peptide film.

15. The method for making a nano-composite gas sensor according to claim 14, wherein the solvent is selected from the group consisting of MEK, IPA, $H_2O$ and PVA.

\* \* \* \* \*